US006439381B1

(12) United States Patent
Alvarez

(10) Patent No.: US 6,439,381 B1
(45) Date of Patent: Aug. 27, 2002

(54) PAINT SAVER

(76) Inventor: John Michael Alvarez, 160 Harding St., Massapequa Park, NY (US) 11762

( * ) Notice: Subject to any disclaimer, the term of this patent is extended or adjusted under 35 U.S.C. 154(b) by 0 days.

(21) Appl. No.: 09/643,425

(22) Filed: Aug. 23, 2000

(51) Int. Cl.[7] .................................... A61F 13/00
(52) U.S. Cl. ..................... 206/229; 206/223; 220/570; 220/23.88
(58) Field of Search ............................ 206/229, 573, 206/223; 220/23.88, 570

(56) References Cited

U.S. PATENT DOCUMENTS

| | | | | | |
|---|---|---|---|---|---|
| 3,225,914 | A | * | 12/1965 | Klein et al. | 206/229 |
| 3,301,267 | A | * | 1/1967 | Geradi et al. | 206/229 |
| 4,384,645 | A | * | 5/1983 | Manfredi | 206/229 |
| 4,756,411 | A | * | 7/1988 | Garland | 220/573 |
| 4,848,946 | A | * | 7/1989 | Goncalves | 206/229 |
| 4,932,552 | A | * | 6/1990 | Wilson | 206/229 |
| 5,080,149 | A | * | 1/1992 | Peoples | 220/573 |
| 5,222,534 | A | * | 6/1993 | Wilkinson, Jr. | 220/513 |
| 5,553,701 | A | * | 9/1996 | Jarecki et al. | 206/229 |
| 5,966,772 | A | * | 10/1999 | Woodnorth et al. | 206/229 |
| 5,979,658 | A | * | 11/1999 | Allen et al. | 206/229 |

* cited by examiner

*Primary Examiner*—Joseph M. Moy

(57) ABSTRACT

The storage of the paint into the quart bottles keeps the paint from drying and developing a skin. There is a rack with bottles that have threads to accommodate the self feed roller and self feed brush that makes it easy for touch-ups and cleaning. This storage system keeps the paint and it's accessories (brushes and rollers) neat and organized.

3 Claims, 5 Drawing Sheets

PAINT SAVER

FIELD OF THE INVENTION

The invention relates to an apparatus and method for storing paint after cans have been open and for quick touch-ups. In particular, the invention concerns an apparatus that stores a variety of used paints in individual containers and provides for paint applicator attachments that are readily connectable to the containers.

BACKGROUND OF THE INVENTION

Paint is commonly sold in gallon containers or cans. Sometimes the paint is sold in five-gallon cans. If properly purchased there should be no more than one quart of paint remaining after the job is completed. When the paint is left in the cans, the cans become rusted, the labels become unreadable and the-paint becomes unusable.

SUMMARY OF THE INVENTION

The present invention provided an apparatus for storing unused paint and performing touching up jobs. The apparatus comprises a rack for storing a plurality of containers, and one or more paint applicators that are readily connectable to the containers. In a preferred embodiment, the paint applicators include a self feed roller and a self feed edge brush. The roller and edge brush each have a cap for connection to each of the containers. In a preferred embodiment, the rack is constructed of plastic. In addition, the containers, self feed roller, and self feed edge brush may also be constructed of plastic. Each container is provided with an identification for the contents therein. The apparatus may also include a funnel for filling the containers with paint remaining in a paint can after the initial job has been completed.

DETAILED DESCRIPTION OF THE INVENTION

Figure 1:
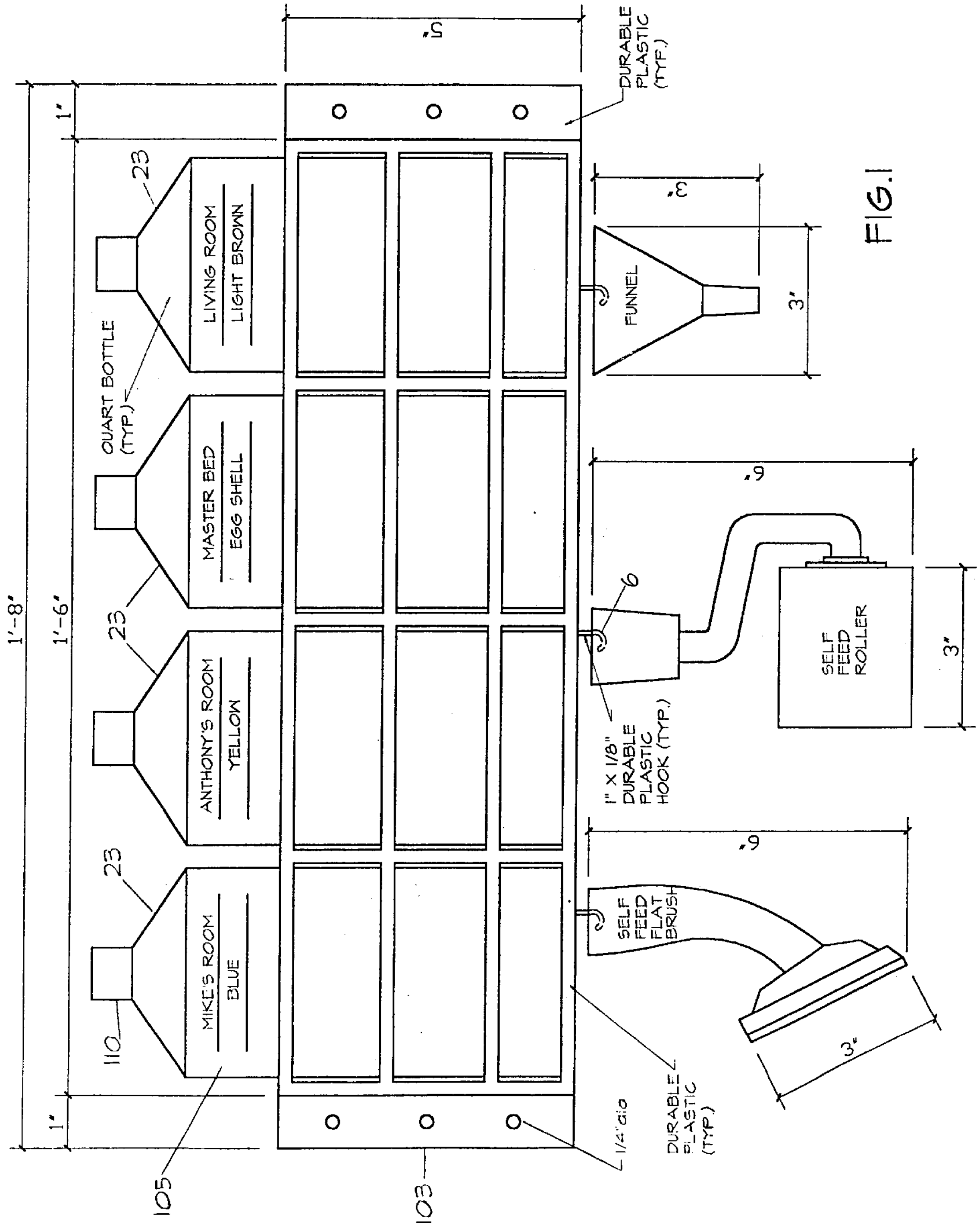
FIG. 1 is a front view of the apparatus of the invention.
Figure 2:
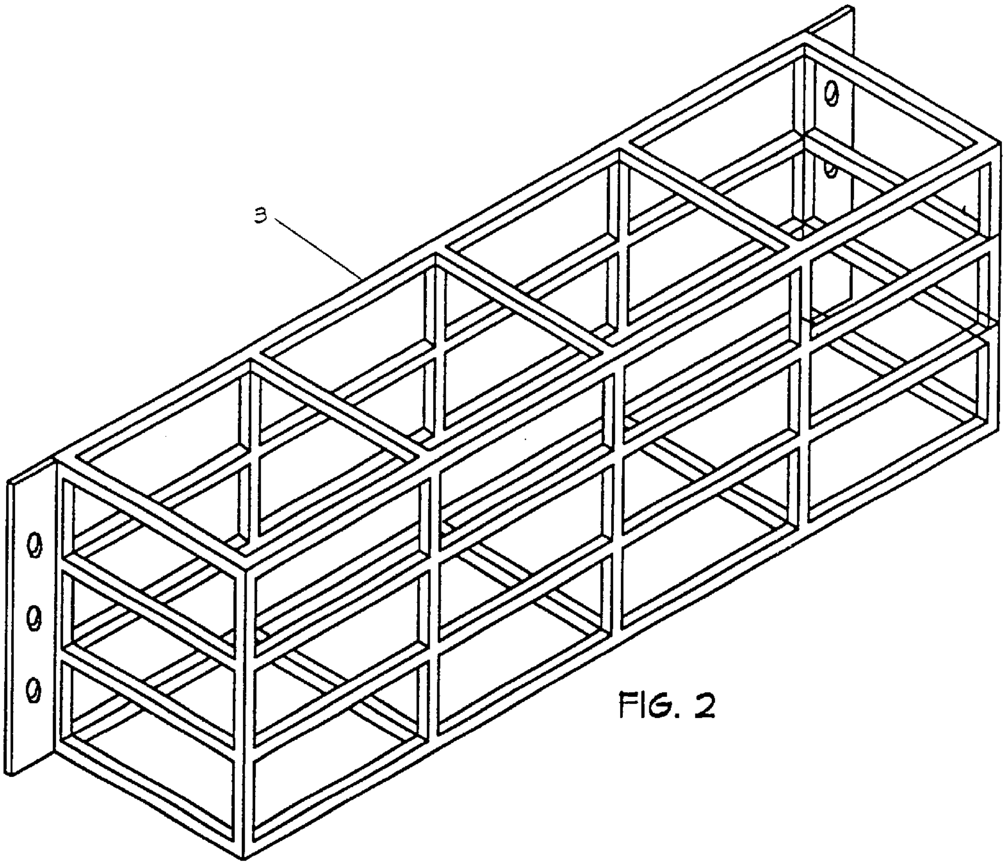
FIG. 2 is a perspective view of the rack of the invention.
Figure 3:
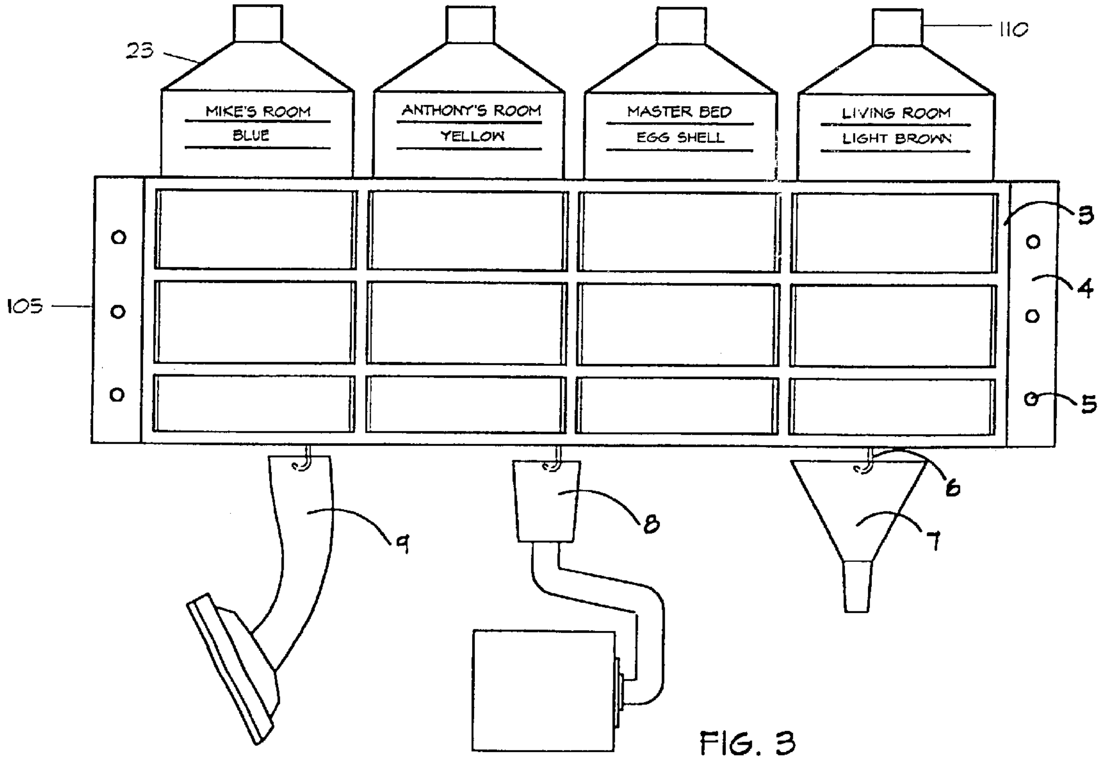
FIG. 3 is another front view of the apparatus shown in FIG. 1.
Figure 4:
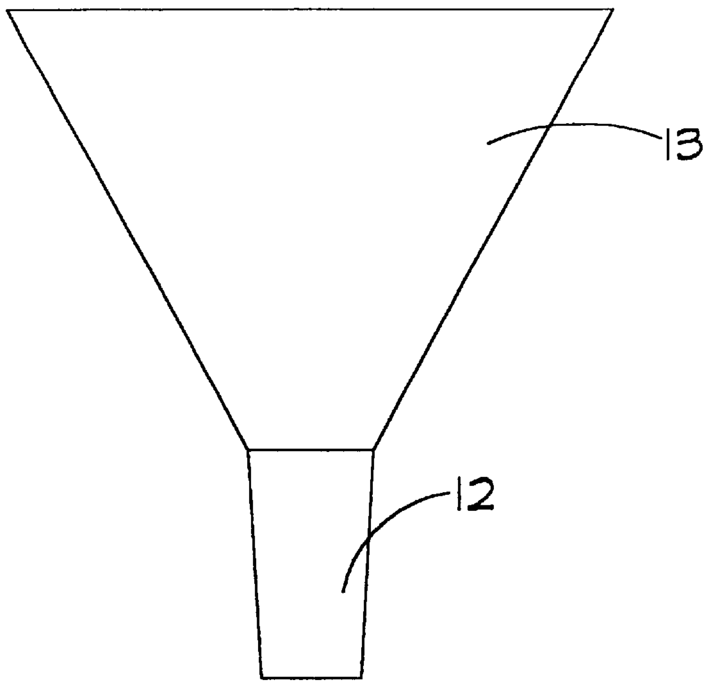
FIG. 4 is a side view of the funnel of the invention.
Figure 5:
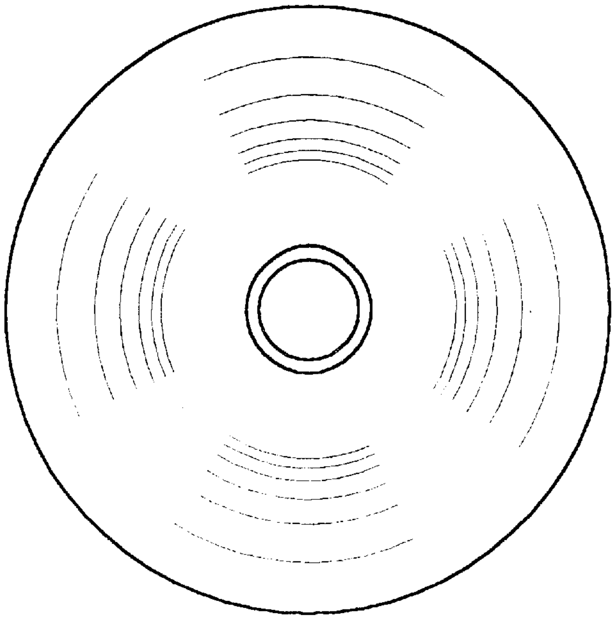
FIG. 5 is a top view of the funnel of the the invention.
Figure 6:
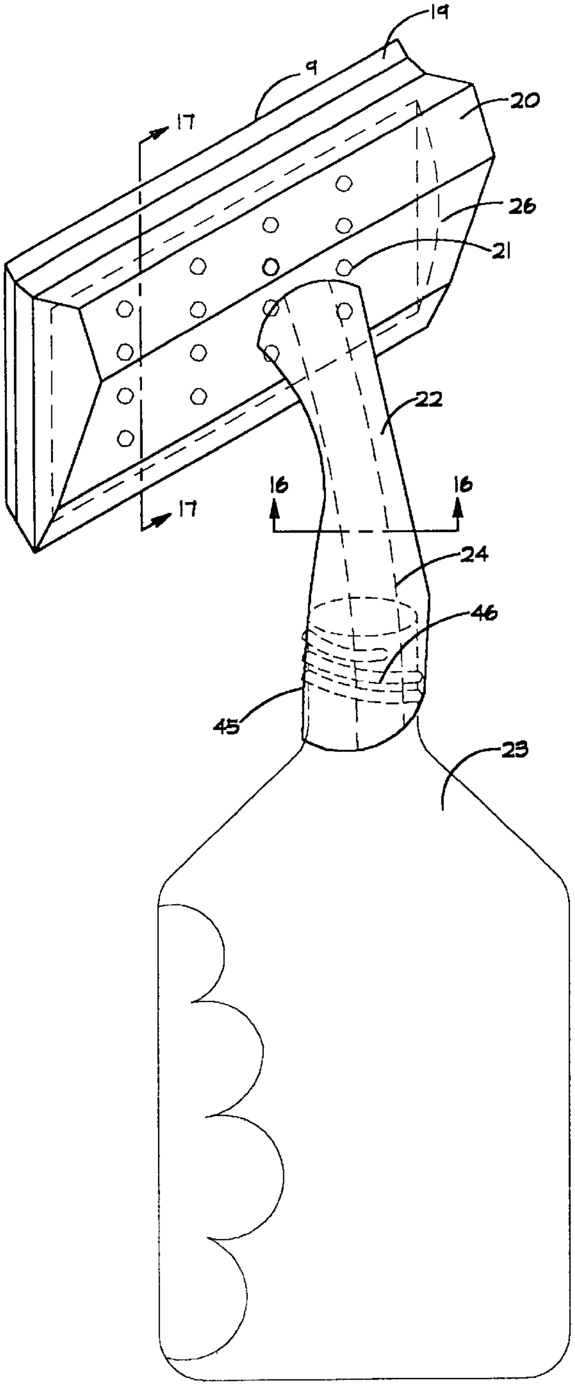
FIG. 6 is a perspective view of the self feeder edge brush of the invention mounted on a plastic bottle shown in lighter print.
Figure 7:
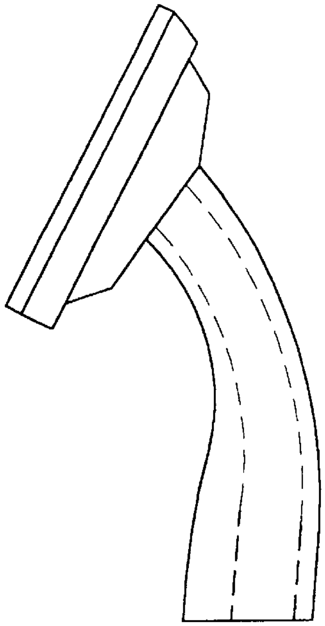
FIG. 7 is a side view of the self feeder edge brush and spout shown in FIG. 6.

Referring to FIGS. 1–5, wherein like reference numbers designate like parts, the apparatus of the invention includes a partially enclosed rack 3 that affords storage space for several plastic bottles 23, of varying size, and attachment hooks 6 on the underside of the rack for the convenient placement and storage of paint brushes 9, rollers 8, and funnel 7. The plastic bottles 23 may be used for storing excess paint that has been used and a label 105 affixed to the bottle 23 identifies the paint color and room/area on which the paint was used. The design reduces wastage of paint and eliminates the need for retaining partially filled paint cans which tend to become rusty and occupy excess storage space, with the contents frequently becoming unusable. The brush 9 and roller 8 are self -feeding to make it easy to touch up walls when necessary with easy clean up.

After initial painting has been accomplished, there is inevitably some excess paint remaining in the can and stored away for future use. Several problems with storing paint in cans include an excessive amount of storage space required, the contents becoming dry and unusable, and the paint cans becoming rusty and unsightly. The apparatus of the invention solves these problems.

In a preferred embodiment, the rack 3 is a rectangular in shape and is enclosed by a back panel, front panel and two side panels. All panels may be manufactured from sturdy, durable plastic material. The rack 100 and other components of the apparatus may be produced in a variety of colors to enable individuals to select a color for matching decor or to suit their own color preferences. Three attachment devices, plastic hooks 6, extend downward from the underside of the bottom panel and are used for hanging a self-feeding paintbrush 9, roller 8, funnel 7 and other paint accessories. Positioned on the inner shelf are several various sized plastic bottles 23.

Referring now to FIGS. 6–14, the bottles 23 are provided with threaded spouts 46. Whenever a painting job has been completed, the excess paint would be funneled into a plastic bottle(s). The room or area in which the paint has been used, and the color of the paint, is written on the label 105 affixed to the bottle for identification. A cap 110 (See FIGS. 1 and 3) is then threaded on the bottle 23 and the bottle is placed on the rack 100 for future use. This method of saving excess paint is much neater than using the original paint cans, reduces waste, and eliminates the necessity of keeping unsightly paint cans. The apparatus also makes touch ups easy. As noted previously, paint that is left in cans frequently becomes dry and hard and is no longer usable. This apparatus of the invention eliminates this problem. Identification would also be a lot easier as many times a paint can is unreadable because of paint splotches on the can. The apparatus of the invention also saves space as well as money.

Production of the apparatus of the invention is fairly straight forward, requiring current plastic molding technology. The materials needed to produce the apparatus are "off-the-shelf" type materials. This simply means they are readily available, competitively priced and meet the standards set by the United States government, i.e., O.S.H.A., EPA, UL, etc. In today's environment the materials used in factories are of considerable importance. With the public awareness of clean air and clean water, the laws governing these areas are strictly enforced. Manufacturers, especially in the plastics industry, are very cautious when it comes to using materials not already environmentally approved.

Referring again to the figures, in a preferred embodiment, the invention includes a heavy plastic rack 3 having dimensions of 1'4¼" long, 3¾" wide, 5" high with four slots for quart bottles 23. Three ¼" round holes 5 on both sides of the rack to fasten to a wall (not shown). The sides 4 of the of the rack are 1" wide, 5" high, and are made of heavy duty plastic. Five ¼" holes 5 are provided on the side brackets. Heavy duty plastic hooks 6 are attached to the bottom of the rack.

A funnel 7 is provided having dimensions 6" high, 3" wide. The apparatus also includes a self feed roller 8, and self feed brush 9. The bottom stem 12 of the funnel is 2½" long and tapered with 1" spout. The top 13 of the funnel is tapered 3" and is 4" long.

Figure 8:
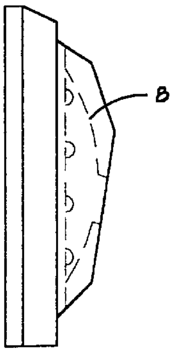
FIG. 8 is a side view of the self feeder edge brush taken along lines 17—17 in FIG. 6.
Figure 9:
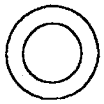
FIG. 9 is a side view of the spout shown taken along lines 16—16 in FIG. 6.
Figure 10:
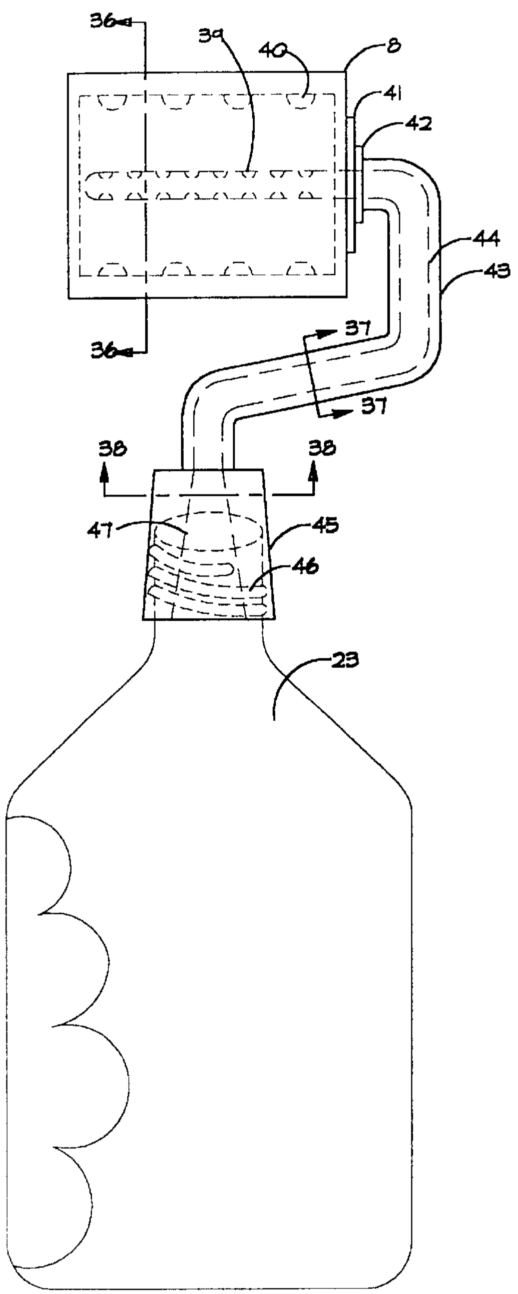
FIG. 10 is a front view of the self feeder roller of the invention mounted on a plastic bottle shown in lighter print.
Figure 11:
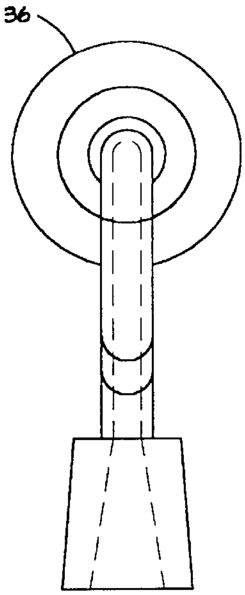
FIG. 11 is a side view of the self feeder roller shown in FIG. 10.
Figure 12:
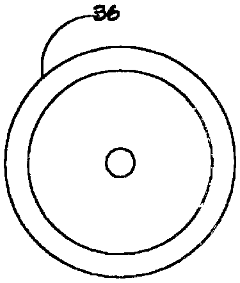
FIG. 12 is cross-section of the roll pad taken along lines 36—36 of FIG. 10.
Figure 13:
FIG. 13 is a cross-section of the self feeder tube taken along lines 37—37 of FIG. 10.
Figure 14:
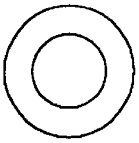
FIG. 14 is a cross-section of the cap of the self feeder roller taken along lines 38—38 of FIG. 10.

Referring to FIGS. 6–9, the self feed edge brush 9, has a plastic tube 22 having an outside dimension of 1 1/16", and a 1" diameter inner tube. The tube 22 is 4½" long to feed the paint to the brush. Referring to FIG. 8, the flat self feed edge brush is 2½" high, and 3" wide. The brush has a slant 20 that is 3¾" long and composed of plastic. A plurality of interior holes 21, each having a diameter of 1/16" feed paint into edge brush. The brush also has a back support 26 with dimensions 1¼" wide and 3" long.

FIGS. 10–14 show various aspects of the self feed roller 8 in accordance with the invention. The roller 8 has a roll pad 36 that is 3" long and 2½" wide. The roller also includes a self feeder tube 37 having outer and inner diameters of ½" outside and ¼" inside. The cap 45 of the bottle has a 1 1/16" outside diameter and an inner tube having a diameter of 1" to feed self feeder tube 37. Holes 39 and 40 feed the paint from the tube feeder 37 to the role pad 36. The diameter of the tube feeder in the vicinity of the holes 39 is ½". A plastic piece 41 that is ⅞" long holds roller 36 on the self feeder. An additional plastic piece 42 that is ⅝" long also holds roller on the self feeder. The outer surface of the tube feeder 37 has a ⅛" thick metal surface 43 that holds roller to the cap and bottle. An inner metal tube 44, ¼" wide is also provided.

DETAILED DESCRIPTION OF "THE PAINT SAVER"

Figure #1 Heavy Plastic Rack 1'4¼" long, 3¾" wide, 5" High with Four Slots for Quart Bottles, Three ¼" Round Holes on both sides of the rack to fasten to wall.

Figure #2 Full View of Paint Saver Rack.

Figure #3 Heavy Duty Plastic, ¼" thick rack.

Figure #4 Sides of rack 1" wide, 5" High made of Heavy Duty Plastic.

Figure #5 Five ¼" holes on side brackets.

Figure #6 Heavy duty Plastic Hooks.

Figure #7 The funnel. Dimensions on figure 10.

Figure #8 Self Feed Roller. Dimensions on figure 34 to figure 47.

Figure #9 Self Feed Edge Brush.

Figure #10 Side View of Funnel, 6" High.

Figure #11 Top View of Funnel, 3" Wide.

Figure #12 Bottom Stem of Funnel, 2½" Long Tapered with 1" spout

Figure #13 3" Tapered top of funnel 4" long.

Figure #14 Omit.

Figure #15 Plastic Bottle 3¼" wide, 9½" High. (same as figure #34).

Figure #16 The outside dimension is 1 1/16"1" inner tube, 4½" long to feed the paint to the brush.

Figure #17 Flat Self feeder edge brush 2½" High, 3" wide.

Figure #18 Side View of self feeder edge brush.

Figure #19 Flat edge Brush Pad 2½" High, 3" Wide.

Figure #20 Slant ¾" plastic piece of edge brush.

Figure #21 1/16" hole to feed paint into edge brush.

Figure #22 Plastic Tube that feeds the paint from the bottle to the brush, 4½" long with slight curve.

Figure #23 Same as figure 15 and figure 34.

Figure #24 The cap of the bottle and the bottom of the brush. It connects the bottle to the brush. (same as figure 38).

Figure #25 Basic threads to accommodate bottle cap. Same as figure 46.

Figure #26 Back support for brush 1¼" wide, 3" long.

Figure #27 Omit for Separate Patent.

Figure #28 Omit for Separate Patent.

Figure #29 Omit for Separate Patent.

Figure #30 Omit for Separate Patent.

Figure #31 Omit for Separate Patent.

Figure #32 Omit for Separate Patent.

Figure #33 Omit for Separate Patent.

Figure #34 Plastic Bottle 3¼" wide, 9½" high.

Figure #35 Side View of Self Feeder Roller.

Figure #36 Roll Pad 3" long, 2½" wide.

Figure #37 Self feeder tube, ½" outside, ¼" inside.

Figure #38 Cap of Bottle, bottom of roller and brush. 1 1/16" Outside inner tube 1" for self feeder.

Figure #39 ½" tube roller

Figure #40 Hole to feed brush.

Figure #41 Plastic piece to hold roller on the self feeder ⅞" long.

Figure #42 Plastic piece to hold roller on the self feeder, ⅝" long.

Figure #43 ⅛" thick metal that holds roller to the cap and bottle.

Figure #44 Inner metal tube for flow of paint ¼" wide.

Figure #45 Cap of bottle connected to self feed roller on self feed brush.

Figure #46 Basic threaded bottle to accommodate cap.

Figure #47 Tube for the self feeder.

What is claimed is:

1. A paint saver apparatus for storing unused paint and performing touching up jobs, comprising:

a rack for storing a plurality of containers;

a funnel;

a self feed roller having cap for connecting the roller to each of the containers; and a self feed edge brush having cap for connecting the roller to each of the containers.

2. A paint saver according to claim 1 in which each containers is provided with a identification for the contents therein.

3. A paint saver according to claim 1 in which the rack is constructed of plastic.

* * * * *